(12) United States Patent
Wynn et al.

(10) Patent No.: US 10,017,434 B2
(45) Date of Patent: Jul. 10, 2018

(54) MEMBRANE-BASED GAS SEPARATION PROCESSES TO SEPARATE DEHYDROGENATION REACTION PRODUCTS

(71) Applicant: Membrane Technology and Research, Inc., Newark, CA (US)

(72) Inventors: Nicholas P Wynn, Redwood City, CA (US); Alvin Ng, Milpitas, CA (US); Douglas Gottschlich, Redwood City, CA (US); Paul Su, Saratoga, CA (US); Meijuan Zhou, Delmar, NY (US); Sylvie Thomas-Droz, Los Altos, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 27 days.

(21) Appl. No.: 15/271,686

(22) Filed: Sep. 21, 2016

(65) Prior Publication Data
US 2017/0008822 A1    Jan. 12, 2017

Related U.S. Application Data

(63) Continuation of application No. 14/099,267, filed on Dec. 6, 2013, now Pat. No. 9,517,981.

(51) Int. Cl.
*B01D 53/22*    (2006.01)
*B01D 53/00*    (2006.01)
(Continued)

(52) U.S. Cl.
CPC ............ *C07C 7/005* (2013.01); *B01D 53/002* (2013.01); *B01D 53/22* (2013.01); *B01D 53/226* (2013.01); *C01B 3/501* (2013.01); *C07C 7/144* (2013.01); *F25J 3/0271* (2013.01); *C01B 2203/0266* (2013.01); *C01B 2203/041* (2013.01); *C01B 2203/043* (2013.01); *C01B 2203/147* (2013.01); *C01B 2203/148* (2013.01); *F25J 2205/80* (2013.01); *F25J 2270/90* (2013.01)

(58) Field of Classification Search
CPC .... B01D 53/002; B01D 53/22; B01D 53/226; B01D 53/229; C07C 7/005; C07C 7/144; C01B 3/501; C01B 2203/147; F25J 2205/80
See application file for complete search history.

(56) References Cited

U.S. PATENT DOCUMENTS 5,256,295 A    10/1993    Baker et al.
5,430,218 A     7/1995    Miller et al.
(Continued)

FOREIGN PATENT DOCUMENTS

CN    102795956 A    11/2012
EP    2505573 A1     10/2012

*Primary Examiner* — Jason M Greene
(74) *Attorney, Agent, or Firm* — Timothy A. Hott; Suk H. Chow

(57) ABSTRACT

Gas separation processes are provided for separating dehydrogenation reaction products from a raw gas stream to recover hydrocarbons, specifically olefins, such as propylene and iso-butene, as well as unreacted feedstock. The processes employ a sequence of partial condensation steps, interspersed with membrane separation steps to raise the hydrocarbon dewpoint of the uncondensed gas, thereby avoiding the use of low-temperature or cryogenic conditions.

20 Claims, 7 Drawing Sheets

(51) Int. Cl.
  *C07C 7/00*    (2006.01)
  *C07C 7/144*   (2006.01)
  *F25J 3/02*    (2006.01)
  *C01B 3/50*    (2006.01)

(56) References Cited

U.S. PATENT DOCUMENTS

| | | | |
|---|---|---|---|
| 5,452,581 A * | 9/1995 | Dinh | C01B 3/501 |
| | | | 62/631 |
| 5,516,961 A | 5/1996 | Miller et al. | |
| 5,675,052 A | 10/1997 | Menon et al. | |
| 5,769,927 A | 6/1998 | Gottschlich et al. | |
| 5,779,763 A | 7/1998 | Pinnau et al. | |
| 5,785,739 A * | 7/1998 | Baker | B01D 53/229 |
| | | | 95/266 |
| 5,979,178 A | 11/1999 | Engler et al. | |
| 5,980,609 A | 11/1999 | Baker et al. | |
| 6,264,828 B1 * | 7/2001 | Baker | C10G 49/007 |
| | | | 208/100 |
| 6,723,231 B1 | 4/2004 | Geus et al. | |
| 7,405,338 B2 | 7/2008 | Brophy et al. | |
| 2012/0078204 A1 | 3/2012 | Butler et al. | |
| 2012/0190904 A1 | 7/2012 | Butler | |

\* cited by examiner

MEMBRANE-BASED GAS SEPARATION PROCESSES TO SEPARATE DEHYDROGENATION REACTION PRODUCTS

CROSS-REFERENCE TO RELATED APPLICATIONS

This application is a continuation and claims the benefit of U.S. application Ser. No. 14/099,267, filed on Dec. 6, 2013 and issued as U.S. Pat. No. 9,517,981 on Dec. 13, 2016, which is hereby incorporated by reference in its entirety.

FIELD OF THE INVENTION

The invention relates to membrane-based gas separation processes. In particular, the invention relates to such processes as used for the recovery of hydrocarbons from dehydrogenation reactions.

BACKGROUND OF THE INVENTION

The demand for propylene increasingly exceeds the supply available from petroleum refining, so a number of on-purpose propylene production processes have been developed. One important process converts propane to propylene by catalytic dehydrogenation. Under suitable conditions of low pressure and elevated temperature, dehydrogenation proceeds according to the reaction:

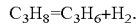

$$C_3H_8 = C_3H_6 + H_2.$$

Most propylene is subsequently converted to polypropylene, a thermoplastic polymer used in a wide variety of applications, and for which the global market exceeds 45 million metric tons.

Likewise, the demand for iso-butene (iso-butylene) exceeds the supply available from refinery streams. On-purpose iso-butylene is manufactured from iso-butane, also by catalytic dehydrogenation at low pressure and elevated temperature, according to the reaction:

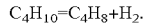

$$C_4H_{10} = C_4H_8 + H_2.$$

Iso-butene is an intermediate in the production of a variety of products. It is reacted with methanol and ethanol in the manufacture of the gasoline oxygenates methyl tert-butyl ether (MTBE) and ethyl tert-butyl ether (ETBE). Polymerization of iso-butene produces butyl rubber (poly-isobutylene).

Industrial dehydrogenation processes are run at low pressure to maximize the conversion of paraffin to olefin. Nevertheless, the per pass conversion is often only around 50%. In this particular case, the reaction product will contain 0.5 mols of olefin, 0.5 mols of co-product hydrogen and 0.5 mols of unreacted paraffin. Side reactions also occur, forming small amounts of lighter hydrocarbons such as ethane and methane. In addition, because the reactions are typically run at sub-atmospheric pressure, ingress of small quantities of air can contaminate the reaction products with nitrogen and oxygen, and some of the oxygen may react to produce water and carbon oxides.

The desired reaction product is commonly recovered from the mixture of product gases by cooling, followed by compression to a pressure at which the least volatile components—the product olefin and the un-reacted feed paraffin—can be condensed out by further cooling. The principal drawback to this process is that, as the olefins and paraffins condense, their partial pressure in the gas stream decreases, lowering the hydrocarbon dewpoint of the gas stream. To achieve high levels of hydrocarbon recovery, therefore, requires deep cooling of the gas stream to temperatures far below the initial dewpoint of the reaction mixture. Temperatures down to as low as −40° C. or below are routinely employed, necessitating costly pretreatment of the gas (to avoid freezing of water vapor and carbon dioxide), costly materials of construction (to avoid embrittlement problems), and expensive and complex ways to provide refrigeration, such as the use of cryogenic turboexpanders.

After very low temperature or cryogenic condensation, the recovered liquid is stabilized by stripping out lighter components and the resultant olefin/paraffin mixture is distilled to separate the olefin product from the unreacted paraffin feed, which is recycled to the reaction step. The uncondensed gases, predominantly hydrogen, are used as fuel or may be further purified, for example by pressure swing adsorption.

Various designs incorporating separation membranes have been proposed for improving dehydrogenation processes.

U.S. Pat. No. 7,405,338, to Brophy et al. (Velocys), discloses a method of dehydrogenating hydrocarbons to yield unsaturated compounds. The method reduces coking in the catalyst bed and allows for stable, relatively long-term operation in small reactors. In some embodiments, a hydrogen-permeable membrane is used to selectively remove hydrogen.

U.S. Pat. Nos. 5,516,961 and 5,430,218, to Miller et al. (Chevron), disclose processes for catalyst dehydrogenation of light paraffinic hydrocarbons using a catalyst comprising a noble metal and an intermediate pore size zeolite having a specified alkali content. The processes may include a membrane separation step for separating hydrogen from the effluent of the dehydrogenation reaction. The polymer-porous solid composite membrane may be, e.g., a porous ceramic material coated with a fluorinated dianhydride-diamine, a fluorinated polycarbonate or fluorinated polysulfone.

U.S. PG Pub. Nos. 2012/0190904 and 2012/0078204, to Butler et al. (Fina Technology, Inc.), disclose dehydrogenation methods that include passing a dehydrogenation product through a membrane separator and permeating hydrogen through a membrane positioned in the membrane separator. In certain embodiments, the membrane is inorganic and formed of either ceramic or a sintered metal.

Chinese Patent Application CN102795956(A), to Wilson Engineering, discloses a method for separating reaction products produced during preparation of propylene by dehydrogenating propane. In the method, reaction products produced during preparation of propylene by dehydrogenating propane are separated by combining membrane separation with cryogenic separation.

European Patent Application EP2505573A1, to Stamicarbon B. V., discloses a process for the catalytic dehydrogenation of alkanes so as to form the corresponding olefins. The reaction mixture is subjected to membrane separation of hydrogen, in a separate unit. Preferably a plurality of alternating reaction and separation units is used. The process of the invention serves the purpose of reducing coke formation on the catalyst, and also of achieving a higher alkane conversion without a similar increase in coke formation. The process can also be used for the production of hydrogen.

Given the huge demand for $C_3$ and $C_4$ olefins, and the complexity and cost of low-temperature and cryogenic operations, it would be highly desirable to improve the product recovery train to avoid the use of low-temperature separation steps as far as possible. There remains an unmet need for processes that can recover light olefins and paraffins from raw reaction mixtures in a simple, cost and energy efficient manner.

SUMMARY OF THE INVENTION

Accordingly, the present invention relates to a process with a defined sequence of partial condensation, membrane separation, and other steps for treating a raw product stream from dehydrogenation of a light hydrocarbon. The process is able to recover unreacted feedstock hydrocarbon in conjunction with the desired dehydrogenation product, without the need to resort to cryogenic operating conditions.

The raw product stream comprises at least one saturated component, one unsaturated component and hydrogen. The saturated component is preferably a light paraffin, such as propane or iso-butane. The unsaturated component is preferably a light olefin, such as propylene or iso-butene.

A basic embodiment for treating the raw product stream comprises the following steps:
(a) compressing the raw product stream to create a compressed stream having a first hydrocarbon dewpoint;
(b) partially condensing the compressed stream, including cooling and separating the compressed stream into a first hydrocarbon condensate stream and a first uncondensed gas stream;
(c) heating the first uncondensed gas stream from step (b);
(d) separating the first uncondensed gas stream from step (c) using a first membrane to remove a hydrogen-rich permeate gas stream and create a hydrocarbon-enriched residue gas stream having a first residue hydrocarbon dewpoint that is within 15° C. of the first hydrocarbon dewpoint; and
(e) partially condensing the residue gas stream, including cooling and separating the residue gas stream into a second hydrocarbon condensate and a second uncondensed gas stream.

Thus, the basic process defined above involves a sequence of condensation/membrane separation/condensation steps. Described in an overall qualitative way, the sequential steps first lower, then raise, then lower the hydrocarbon dewpoint of the gas under treatment. The use of one or more membrane steps to raise the dewpoint offsets the lowering brought about by condensation, thereby avoiding the need to go to progressively lower condensation temperatures to achieve good hydrocarbon recovery.

Cooling is performed in steps (b) and (e) using a suitable coolant. In the case of propane dehydrogenation, the preferred coolant is water or a refrigerant. In the case of iso-butane dehydrogenation, the preferred coolant is water. The type of coolant used in steps (b) and (e) are preferably the same.

The compressed stream of step (b) and the residue stream of step (e) are each cooled to condense a significant portion of the $C_{3+}$ hydrocarbons contained therein. Expressed in terms of dewpoint reduction, condensation steps (b) and (e) typically lower the dewpoint of the compressed stream and the residue stream by between about 20° C. and 50° C.

Expressed in terms of a specific temperature, both streams are preferably cooled to a temperature no lower than −30° C., and more preferably no lower than −20° C., or even 0° C. Therefore, another basic embodiment for treating the raw product stream may comprise the following steps:
(a) compressing the raw product stream to create a compressed stream having a first hydrocarbon dewpoint;
(b) partially condensing the compressed stream, including cooling the compressed gas stream to a temperature no lower than −30° C. and separating the compressed stream into a first hydrocarbon condensate stream and a first uncondensed gas stream;
(c) heating the first uncondensed gas stream from step (b);
(d) separating the first uncondensed gas stream from step (c) using a first membrane to remove a hydrogen-rich permeate gas stream and create a hydrocarbon-enriched residue gas stream having a first residue hydrocarbon dewpoint; and
(e) partially condensing the residue gas stream, including cooling the residue gas stream to a temperature no lower than −30° C. and separating the residue gas stream into a second hydrocarbon condensate and a second uncondensed gas stream.

In step (b), the condensation of the compressed stream lowers the dewpoint of the first uncondensed gas stream. An important objective of the present invention is to reverse or substantially reverse this dewpoint lowering by using one or more membrane steps. After the first uncondensed gas stream is heated in step (c), the membrane separation in step (d) preferentially removes hydrogen, thereby increasing the hydrocarbon-enriched residue stream dewpoint, typically between about 20° C. and 50° C.

The membrane separation of step (d) thus results in a hydrocarbon-enriched residue stream having a first residue hydrocarbon dewpoint that is roughly the same (within plus/minus 20° C.) of the first hydrocarbon dewpoint of the compressed stream from step (a). In certain embodiments, the first residue hydrocarbon dewpoint is more preferably within 15° C., and most preferably with 10° C. of the first hydrocarbon dewpoint.

Membranes for use in step (d) of the process of the invention may comprise any material suitable for preferentially permeating hydrogen over hydrocarbons. In certain embodiments, the membrane preferably exhibits a hydrogen permeance of at least 200 gpu.

In the case of propane or iso-butane dehydrogenation, the membrane preferably has a selectivity for hydrogen over the paraffin of at least about 30, and more preferably at least about 100.

Other variations of this process may be implemented in order to increase hydrocarbon recovery.

In certain embodiments, the process comprises the steps (a)-(c), above, and the additional steps of:
(f) separating the second uncondensed gas stream from step (e) using a second membrane to remove a hydrocarbon-rich permeate gas stream; and
(g) recompressing and recirculating the hydrocarbon-rich permeate gas stream to step (b).

In certain embodiments, the process comprises the steps (a)-(e), above, and the additional step of:
(f) recirculating at least a portion of the second uncondensed gas stream to step (c).

In certain embodiments, the processes described above may also be used to recover high-purity hydrogen by pressure swing adsorption (PSA). The hydrogen-rich permeate gas stream from step (d) is treated by a PSA unit to remove a high-purity hydrogen product stream and create a hydrocarbon-enriched tail gas stream. The tail gas may then be recompressed and recirculated to step (c).

It is to be understood that the above summary and the following detailed description are intended to explain and illustrate the invention without restricting it in scope.

DETAILED DESCRIPTION OF THE INVENTION

The term dewpoint as used herein refers to the hydrocarbon dewpoint unless specifically stated otherwise.

The terms low-temperature condensation, low-temperature refrigeration and low-temperature cooling refer to operations conducted under deep refrigeration or cooling conditions at temperatures below −30° C.

Gas percentages and ratios given herein are molar unless stated otherwise.

Pressures as given herein are in bar absolute unless stated otherwise.

The invention is a process for treating a raw product gas from a dehydrogenation reaction. The process is particularly useful in treating raw gas from dehydrogenation of light or low-boiling (boiling point below 0° C.) saturated hydrocarbons, and especially from dehydrogenation of light paraffins, such as propane and iso-butane.

As mentioned in the background section above, the raw product gas typically contains many components. As a representative, non-limiting example, the composition may be from 20% to 40% hydrogen, 20% to 40% olefin product, 20% to 40% unreacted paraffin, and up to 5-10% of methane, nitrogen, carbon oxides and other gases.

The invention involves subjecting this multicomponent raw gas to a defined sequence of partial condensation and membrane separation steps. The condensation steps remove hydrocarbon condensate from the raw product stream, leaving an uncondensed stream of much lower hydrocarbon dewpoint. The membrane separation step(s) are used to raise the hydrocarbon dewpoint back to a value comparable with the pre-condensation value. In this way, the need to resort to progressively lower temperatures for each condensation step is avoided, and the process as a whole can be carried out to achieve good hydrocarbon recovery without the need for low-temperature or even cryogenic processing.

Figure 1:
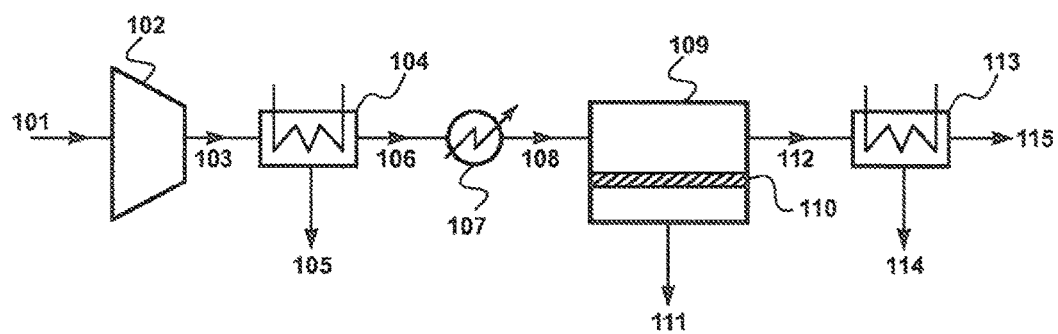
FIG. 1 is a schematic drawing showing a process flow scheme for a basic embodiment of the invention using two partial condensation steps and one membrane separation step.

A basic process according to the invention is shown in FIG. 1.

It will be appreciated by those of skill in the art that FIG. 1 and the other figures showing process schemes herein are very simple block diagrams, intended to make clear the key unit operations of the embodiment processes of the invention, and that actual process trains may include many additional steps of a standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from process to process.

Referring to FIG. 1, raw product stream 101 emanates from the dehydrogenation reactor(s). Optionally, stream 101 may already have been subjected to preliminary treatment, such as cooling or impurity removal, after leaving the reactors and before entering the process of the invention.

Stream 101 is typically at relatively low pressure, and may be at below atmospheric pressure, depending on the specific conditions under which the dehydrogenation process is carried out and whether it has been subjected to any preliminary processing before entering the process of the invention.

Stream 101 is routed to compression step, 102, the goal of which is to compress the stream to a pressure under which the hydrocarbon product and unreacted feedstock may be condensed in the subsequent process steps. Because of the process features discussed below, this pressure need not be very high, and is usually a few tens of bar. It is preferred that the pressure to which the raw product stream is raised be no more than about 40 bara, and more preferably no more than about 35 bara. Ideally, for propane dehydrogenation the raw product stream pressure is about 30 bara; in iso-butane dehydrogenation, the raw product stream pressure is ideally about 20 bara.

The compression step may be carried using compressor equipment of any convenient type, and may be performed in one step or in a compression train of multiple sub-steps, depending on the degree of compression needed.

The raw product stream emerges from step 102 as compressed stream, 103. This stream is sent to first partial condensation step, 104. The condensation step includes cooling of stream 103 to below its hydrocarbon dewpoint temperature, such that a major portion of the hydrocarbon is condensed, followed by separation of the resulting liquid and gas phases.

Cooling may be performed in any manner, and in one or more sub-steps, including, but not limited to, simple air or water aftercooling of the compressor outlet gases, heat exchange against water or other on-site process streams, chilling by external refrigerants, and any combinations of these. Such methods are familiar to those of skill in the art.

A feature of the invention is the iterative and integrated condensation and membrane separation steps. Use of these steps in the manner described herein enables the first, and indeed all, condensation steps in the process to be carried out without resorting to the use of low-temperature or even cryogenic operations and their attendant complications. Thus, step 104 can, and should most desirably be, carried out to achieve only modest cooling of stream 103. Preferably, therefore, this step should cool stream 103 to a temperature no lower than −30° C., and yet more preferably to no colder than about −20° C., 0° C., or even 15° C.

The liquid and gas phases that are formed by compression and cooling are separated by conventional means in a knock-out drum or the like to yield organic liquid stream, 105, and uncondensed stream 106. The organic liquid stream 105 is a principal product stream of the process. This stream typically contains 80 mol %, 90 mol % or more of the combined feedstock and desired reaction products, and may be sent to downstream fractionation treatment to separate the feedstock (for ultimate return to the dehydrogenation reactor), from the unsaturated product, which may be routed to any desired destination or use.

By preferentially removing substantial amounts of hydrocarbon components, the condensation step lowers the dewpoint of the uncondensed gas stream, 106, typically by about 20-50° C. The goal of membrane separation step, 109, is to reverse this decline by preferentially removing hydrogen, thereby elevating the hydrocarbon dewpoint of stream 112, preferably back to a level at least roughly comparable with that of stream 103.

Before this can be done, it is desirable to pass stream 106, through heating step, 107, to avoid subsequent condensation of hydrocarbons within the membrane modules as hydrogen is progressively removed from the stream. Heating step 107 may be carried out in any way, for example by heat exchange with suitable hot streams if available on-site, or with steam.

Heated stream, 108, forms the feed stream to membrane separation step, 109. This step is carried out in a membrane unit containing membranes, 110, that are selectively permeable to hydrogen over hydrocarbons. The membranes preferably have a selectivity for hydrogen over the unsaturated product of at least about 30, more preferably greater than 100, and a hydrogen permeance of at least about 200 gpu.

Any membrane with suitable performance properties may be used in the membrane separation step. The membrane may take the form of a homogeneous film, an integral asymmetric membrane, a multilayer composite membrane, a membrane incorporating a gel or liquid layer or particulates, or any other form known in the art.

Representative preferred polymeric membranes have a selective layer based on a polyimide or a polyimide derivative. Other polymeric materials suitable for the selective layer include polybenzimidazole and its derivatives, and polybenzoxazole. Representative materials suitable for inorganic membranes include metals, metal alloys, and ceramics of various types. Yet other suitable membranes include dense ion-transport membranes or proton-conducting membranes.

The membranes may be manufactured as flat sheets or as fibers and housed in any convenient module form, including spiral-wound modules, plate-and-frame modules, and potted hollow-fiber modules. The making of all these types of membranes and modules is well-known in the art.

Membrane step 109 may be carried out using a single membrane module or bank of membrane modules or an array of modules. A single unit or stage containing one or a bank of membrane modules is adequate for many applications. If either the residue or permeate stream, or both, requires further hydrogen removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

Step 109 can be operated by any mechanism that provides a driving force for transmembrane permeation. Most commonly, this driving force is provided by maintaining a pressure difference between the feed and permeate sides, or by sweeping the permeate side continuously with a gas that dilutes the permeating species, both of which techniques are well known in the membrane separation arts.

FIG. 1 shows a simple pressure-driven case. Stream 108 remains at substantially the same pressure as stream 103, subject only to any small pressure losses through the intervening steps and piping, and is preferably introduced to the membrane modules without pressure adjustment. Less preferably, for example if substantial pressure losses have occurred for some reason, the pressure of stream 108 may be increased before the gas enters the membrane unit. Thus, the feed side is preferably maintained at a few tens of bar, such as 15, 20 or 30 bara. The permeate side is maintained at a lower pressure so as to provide a pressure ratio (total feed pressure/total permeate pressure) of at least about 2, 3, 4 or 5. On the other hand, it is desirable if possible to maintain the permeate pressure at a few bar above atmospheric pressure to facilitate downstream routing, treatment or use of the permeate stream. Thus, the permeate pressure is typically about 2, 3, 5 or 8 bara, by way of non-limiting example.

Returning to FIG. 1, stream 108 flows across the feed side of the membranes 110. A residue stream, 112, that is depleted in hydrogen relative to stream 108, is withdrawn from the feed side of the membrane. The permeate stream, 111, is enriched in hydrogen compared with the membrane feed.

Those of skill in the art will appreciate that it is possible in principle to operate the membrane separation step at a very low stage cut (ratio of total permeate flow to total feed flow), so as to obtain a hydrogen stream of high purity (95+% hydrogen or even 98+% hydrogen) as a permeate product. In this case however, the residue stream will still contain relatively large amounts of hydrogen, and will as a result have a low dewpoint and will necessitate the use of undesirably low temperatures for any further hydrocarbon condensation steps.

We prefer to operate the membrane separation step so as to remove more hydrogen from the feed stream into the permeate stream, thereby raising the hydrocarbon dewpoint of the residue stream. In our process, the hydrocarbon dewpoint of stream 112 should preferably be raised back to a level that is comparable with the dewpoint of stream 103. By this we mean that the dewpoint of stream 112 is within 20° C., more preferably within 15° C., and most preferably within 10° C. of the dewpoint of stream 103. As a consequence of meeting the dewpoint goal, the concentration of hydrogen in stream 111, although high, is typically lower than 95 mol %, and more usually is in the range about 80-90 mol %. Expressed in terms of stage cut, the stage cut in the process of the invention is usually at least about 30% or 40%.

Residue stream 112 is withdrawn from step 109 and directed to second partial condensation step, 113. In general the methodology, options and preferences expressed above with respect to first condensation step 104 apply also to step 113. An important feature of the invention is that the condensation temperature in step 113 is high enough that cryogenic operation and equipment is avoided. Typically and preferably, this condensation temperature is above about −30° C., and yet more preferably is no colder than −20° C., 0° C., or even 15° C.

The condensation temperature in second condensation step 113 may be higher or lower than the condensation temperature in the first condensation step. However, as the dewpoint of stream 112 is the same or similar to the dewpoint of stream 103, the condensation temperature for step 113 is usually the same or similar to the condensation temperature for step 104. As a result, it is convenient and preferred to carry out the second step using the same coolant as is used for the first step. For example, if cooling water is available, it is preferred to cool both streams 103 and 112 using water as coolant. Likewise, if refrigeration is used to cool stream 103, it is preferred to use the same refrigeration source to cool stream 112.

After cooling and separation, step 113 yields a second organic condensate stream, 114, and an off-gas stream or purge stream, 115. Like first condensate stream 105, second condensate stream 114 usually contains at least 80 or 90 mol % of combined feedstock/desired reaction products. This stream may also be fractionated into unsaturated product and saturated feedstock, either separately or by combining with stream 105. Taken together, steps 104 and 113 are able to achieve high levels of recovery of both the unused feedstock and the desired reaction product(s), typically exceeding 85%, and preferably reaching 90% or above.

Purge stream 115 contains hydrogen, minor amounts of unrecovered feedstock and product, and comparatively high concentrations of methane and the other contaminant gases. In this example, the stream is discharged from the process and can be sent to the fuel header.

Figure 2:
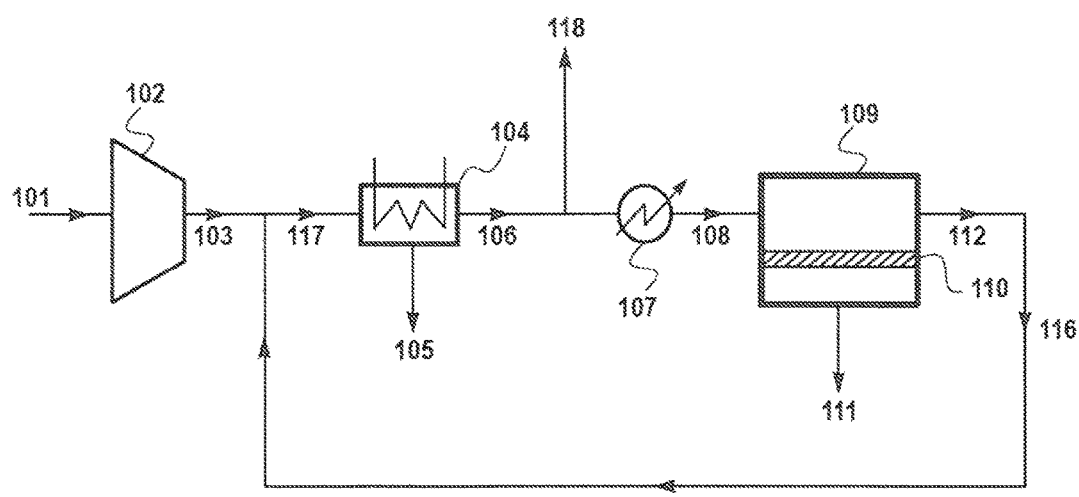
FIG. 2 is a schematic drawing showing a process flow scheme for a variant of the process of FIG. 1, in which the membrane residue stream is recirculated to the initial partial condensation step.

The embodiment of FIG. 1 relies on condensing streams 105 and 114 as separate condensate streams. A variant of this process is shown in FIG. 2, in which like elements are numbered as in FIG. 1. In this case, instead of passing residue stream 112 to a second partial condensation step, the stream is recirculated as stream 116 and combined with stream 103 upstream of condensation step 104. The combined stream, 117, is then passed to the condensation step, so that a single liquid organic condensate stream 105 is produced.

The embodiment of FIG. 2 is simpler than that of FIG. 1 in that only one condenser (typically just the aftercooler system for the initial compressor) is needed. On the other hand an extra blower or compressor is needed to recirculate stream 116. However, the compression requirements for this are modest, resulting only from frictional losses in the equipment and piping. A pressure ratio less than 1.1 will typically suffice, and allows use of a simple single wheel compressor, without aftercooling.

Contaminants are purged from the residue recirculation loop by withdrawing a purge stream, 118, from the loop. This purge stream may be withdrawn from any convenient point in the loop. To minimize hydrocarbon losses into the purge stream, it is preferred to withdraw the purge after the condensation step, where the hydrocarbon concentration in the gas is low.

If a higher degree of hydrocarbon recovery is required than can be achieved by the processes of FIG. 1 and FIG. 2, additional membrane separation and partial condensation steps may be added to increase recovery. For example, if each condensation step is operated at conditions that result in 60% recovery hydrocarbon recovery, then a process using two condensation steps could recover at most (60+24)=84% hydrocarbons, even if essentially no hydrocarbon loss into the membrane permeate stream were to take place. Adding a third condensation step, however, could add up to another 8 or 9% of recovery, and adding a fourth step could add another 4 or 5%, and so on. The amount of contaminant gases in the reactor effluent will limit how far this incremental process can be pushed. Hydrogen permeates the membranes faster than the contaminant gases, which will become concentrated in the remaining gas, eventually increasing co-permeation of hydrocarbons, and resulting in diminishing hydrocarbon recovery.

Figure 3:
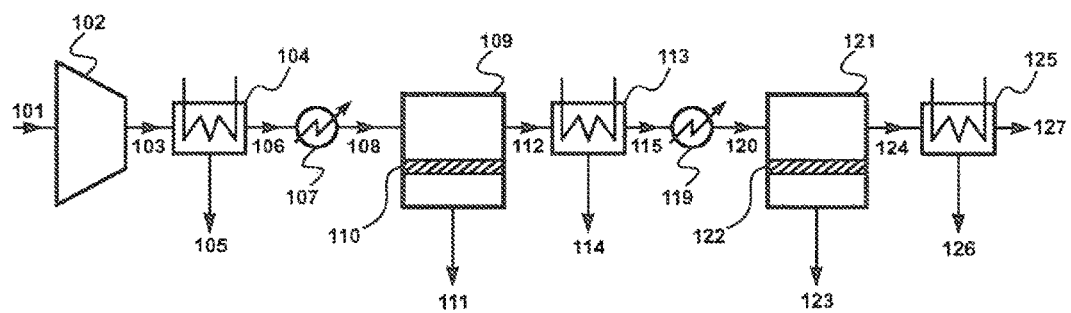
FIG. 3 is a schematic drawing showing a process flow scheme for an embodiment of the invention including three partial condensation steps and two membrane separation steps.

A process using three partial condensation steps is shown in FIG. 3, in which like elements are numbered as in FIG. 1. In this embodiment, uncondensed stream 115 is reheated in second heating step, 119, and then passed as heated feed stream, 120, into second membrane separation step, 121. The methodology, options and preferences expressed above with respect to first membrane separation step 109 and membranes 110 apply also to second membrane separation step 121 and membranes, 122.

Step 121 removes hydrogen from stream 120, and second hydrogen-rich permeate stream, 123, is withdrawn, thereby resulting in a second residue stream, 124, the dewpoint of which has been raised to again be comparable with the dewpoint of stream 103.

Stream 124 is directed to third partial condensation step, 125. The operating conditions and preferences for this step are the same as for the previous condensation steps. In other words, this step operates without resorting to low-temperature refrigeration and conditions. Step 125 produces a third organic condensate stream, 126, which may be fractionated to separate the recovered feedstock from the unsaturated product, and off-gas stream, 127, which may be sent to the fuel header.

Figure 7:
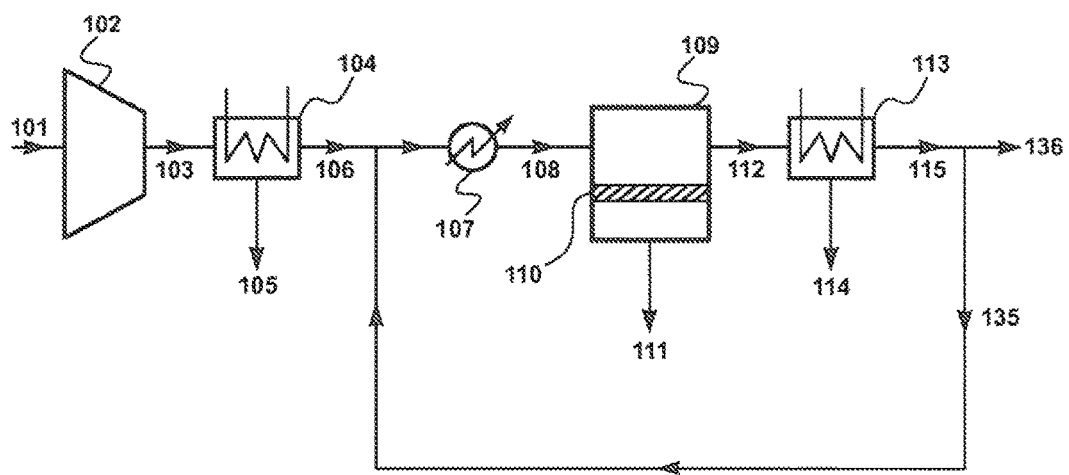
FIG. 7 is a schematic drawing showing a process flow scheme for a variant of the process of FIG. 3, in which uncondensed gas from the second partial condensation step is recirculated to the membrane separation step.

A variant of the process of FIG. 3 is shown in FIG. 7, in which like elements are numbered as in FIG. 1. In this case, instead of passing uncondensed stream 115 to a second membrane separation step, the stream is recirculated as stream 135 and combined with stream 106 upstream of heating step 107. The combined stream, 108, is then passed to the membrane separation step.

Contaminants are purged from the recirculation loop by withdrawing an off-gas stream or purge stream, 136, from the loop.

Figure 4:
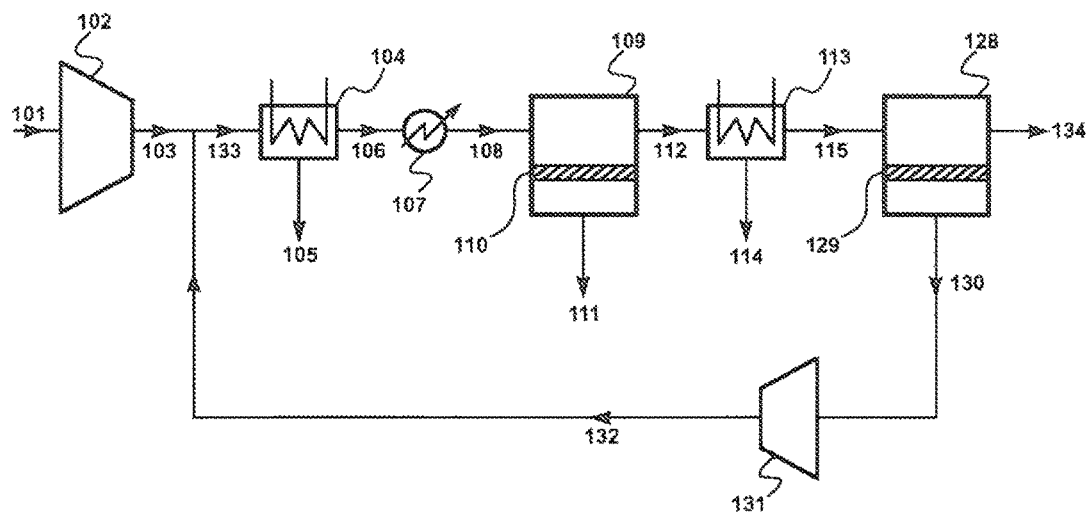
FIG. 4 is a schematic drawing showing a process flow scheme for an embodiment of the invention including a hydrocarbon-selective membrane separation step.

Another option for increasing hydrocarbon recovery is shown in FIG. 4, in which like elements are numbered as in FIG. 1, and in which the same options and preferences as for FIG. 1 generally apply. Referring to FIG. 4, instead of discharging stream 115 from the process, this stream is passed as feed stream to second membrane separation step, 128. Step 128 is carried out using membranes, 129, that are preferentially selective in favor of hydrocarbons over hydrogen. Representative, non-limiting types of membranes that may be used for this step are those having a selective layer of silicone rubber.

Step 128 produces a permeate stream, 130, that is enriched in hydrocarbons compared with stream 115. Stream 130 is recompressed, either in separate recompression step, 131, to form recompressed stream, 132, as shown, or by returning stream 130 to compression step 102, and passes with stream 103 as combined stream, 133, to first condensation step 104.

After treatment in membrane separation step 128, residue stream, 134, has a very low content of feedstock/product hydrocarbons, enabling high recovery rates to be obtained with this design.

Figure 5:
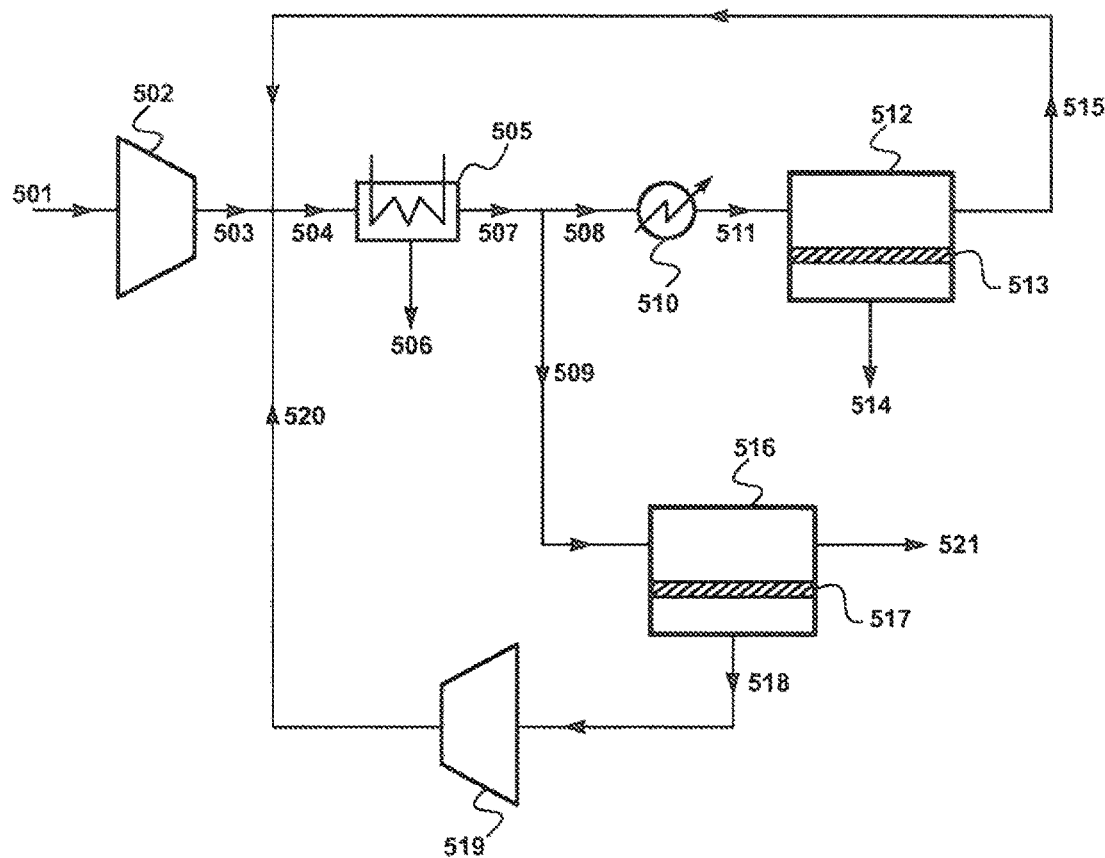
FIG. 5 is a schematic drawing showing a process flow scheme for an embodiment of the invention in which uncondensed gas from the initial partial condensation step is split into a portion that is treated in a hydrogen-selective membrane separation step and a portion that is treated in a hydrocarbon-selective membrane separation step.

An alternative process configuration using hydrocarbon-selective membranes to treat the purge gas to recover additional hydrocarbons is shown in FIG. 5. This embodiment is similar to that of FIG. 2, in that a purge gas stream, 509, is withdrawn from a loop formed by recirculating the membrane residue stream, and is taken from the uncondensed gas. Unless stated otherwise, options and preferences for the various unit operations and the streams entering and leaving them in this figure are the same as in the embodiments of FIG. 1 and FIG. 4.

Referring now to FIG. 5, raw product stream, 501, is compressed in compression step, 502, to form compressed stream, 503. This stream is mixed with streams 515 and 520, discussed below, to form stream 504, which is routed to partial condensation step, 505. This step produces hydrocarbon condensate stream, 506, and uncondensed stream, 507.

Stream 507 is split into two portions. The major portion, 508, is routed to heating step, 510, and then passes as heated stream, 511, to membrane separation step, 512. This step is carried out using membranes, 513, that are selective in favor of hydrogen over hydrocarbons, and produces hydrogen-enriched permeate stream, 514, and hydrogen-depleted residue stream, 515, which is recirculated to condensation step 505.

The minor portion, 509, of stream 507, is withdrawn from the loop formed by recirculating the residue stream from the hydrogen-selective membrane separation step as a raw purge gas stream. Rather than discharging this purge gas stream as in FIG. 2, it is sent to membrane separation step, 516, which is carried out using membranes, 517, that are selective in favor of hydrocarbons over hydrogen. This step produces hydrocarbon-enriched permeate stream, 518, which is recompressed in recompression step, 519, and returned as stream, 520, to the condensation step. In the alternative, stream 518 could be directed to step 502 for recompression. Residue stream, 521, is discharged as a treated purge gas from the process. The use of recycle loops after both membrane separation steps results in increased hydrocarbon recovery levels, typically in excess of 95% or even 97 or 98%.

The most hydrogen-rich streams produced by the processes of the invention as exemplified in the embodiments of FIGS. 1-5 and FIG. 7 are the permeate streams from the hydrogen selective membranes. As was discussed previously, the goal of the membrane separation step is not to achieve high purity for the permeate stream, but to create a residue stream of suitably elevated hydrocarbon dewpoint. Nevertheless, the permeate streams from any of these embodiments typically contain 80 mol % or more of hydrogen, and can be a useful source of hydrogen.

Figure 6:
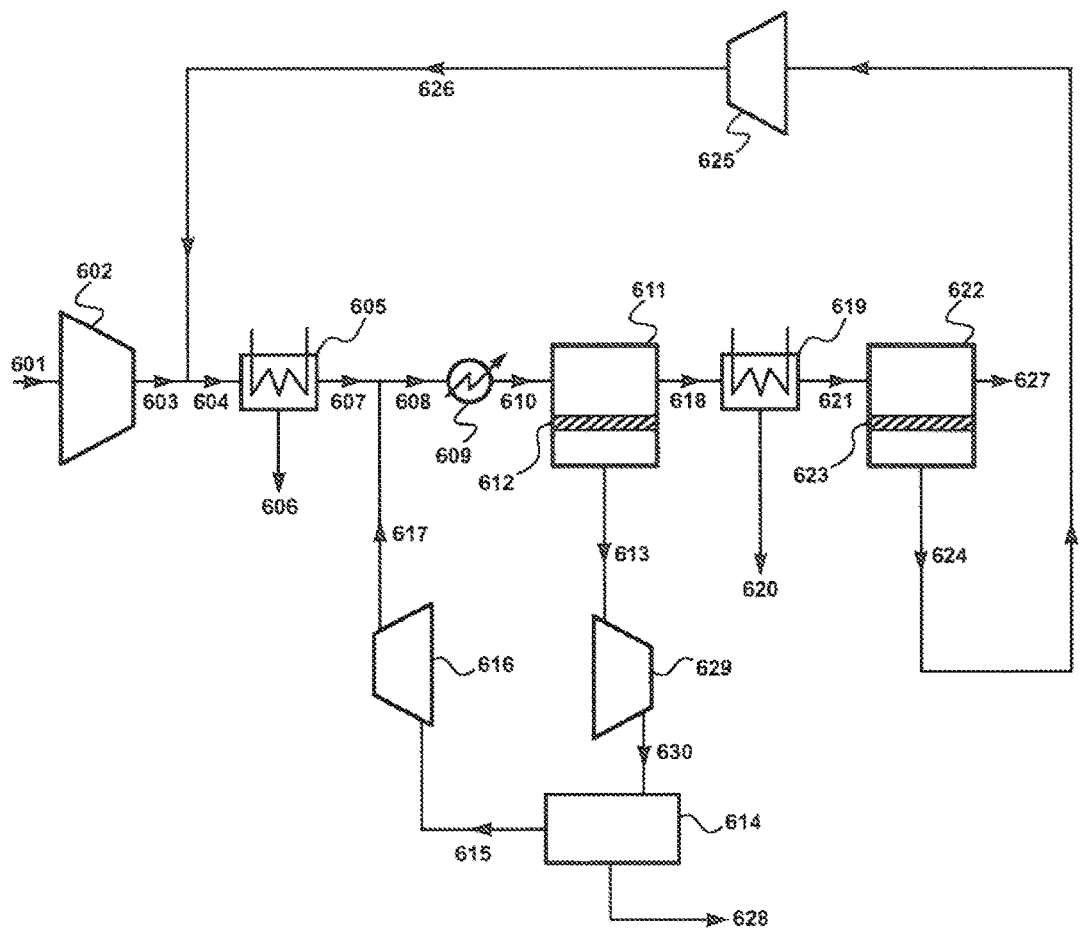
FIG. 6 is a schematic drawing showing a process flow scheme for an embodiment of the invention incorporating a pressure swing adsorption step.

An embodiment in which the membrane permeate stream is further treated by pressure swing adsorption (PSA) to recover high-purity hydrogen is shown in FIG. 6, in which options and preferences for the various unit operations and the streams entering and leaving them are the same as in the embodiment of FIG. 1 unless stated otherwise. FIG. 6 is a representative example based on the process scheme of FIG. 4. It will be clear from the teachings herein that similar variants of the processes of FIGS. 1, 2, 3, 5 and 7 including a PSA step are also possible within the scope of the invention.

Referring to FIG. 6, raw product stream, 601, is compressed in compression step, 602, to form compressed stream, 603. This stream is mixed with stream 626, discussed below, to form stream 604, which is routed to partial condensation step, 605. This step produces hydrocarbon condensate stream, 606, and uncondensed stream, 607.

Stream 607 is combined with stream 617, discussed, below, to form stream, 608, which is routed to heating step, 609, and then passes as heated stream, 610, to membrane separation step, 611. This step is carried out using membranes, 612, that are selective in favor of hydrogen over hydrocarbons, and produces hydrogen-enriched permeate stream, 613, and hydrogen-depleted residue stream, 618.

Residue stream 618 is passed to second partial condensation step, 619, to form second condensate stream, 620, and second uncondensed stream, 621. Stream 621 is passed as feed to second membrane separation step, 622, which is carried using membranes, 623, that are selective in favor of hydrocarbons over hydrogen. This step produces hydrocarbon-enriched permeate stream, 624, which is recompressed in recompression step, 625, and returned as stream, 626, to the first condensation step. In the alternative, stream 624 could be directed for recompression to step 602. Residue stream, 627, is discharged from the process.

Hydrogen-rich permeate stream 613 is compressed in compression step 629 and passed as compressed stream, 630, to a pressure swing adsorption (PSA) step, 614. This step produces a high purity hydrogen stream, 628, which typically contains 99+% hydrogen. Regeneration of the sorption beds produces tail gas stream, 615, which is recompressed in recompression step, 616, and returned as recompressed stream, 617, to form part of the feed to membrane separation step, 611.

Besides recovering a stream of high purity hydrogen, embodiments such as that of FIG. 6 that include a PSA step for hydrogen recovery from the membrane permeate stream(s) enable the operating conditions for the relevant membrane separation steps to be relaxed. As a non-limiting example, it might be desirable in a specific situation, absent the PSA step, to operate membrane separation step 611 at a pressure ratio of 6-10, to limit losses of hydrocarbon into permeate stream 613 plus achieve a suitably elevated dew-point for stream 618. When the PSA step is added, more hydrocarbon can be lost into the permeate stream, as this hydrocarbon will ultimately be recovered by recirculating the PSA tail gas. Hence it may be possible to operate step 611 at a lower pressure ratio of just 2 or 3. This means that the pressure on the permeate side can remain higher, perhaps at 5 or 10 bara, limiting the extra compression needed to run the PSA step.

The invention is now further described by the following examples, which are intended to be illustrative of the invention, but are not intended to limit the scope or underlying principles in any way.

EXAMPLES

Example 1. Embodiment of FIG. 1, Applied to Propane Dehydrogenation

A calculation was performed to model the performance of the process of FIG. 1 in treating a raw product stream from a propane dehydrogenation process. The stream flow rate was assumed to be 5,000 kmol/hour, and the molar composition was assumed to be approximately as follows:
Hydrogen: 30%
Propane: 36%
Propylene: 27%
$C_1$ and $C_2$: 4.5%
Other contaminants (nitrogen, CO, $C_4$): 3%.

It was further assumed that the raw product stream was compressed to 30 bara in compression step 102, then cooled using cooling water to 15° C. in first condensation step 104. The membrane was assumed to have a hydrogen permeance of 700 gpu, a hydrogen/propane selectivity of 40 and a hydrogen/propylene selectivity of 30. The overhead stream from step 104 was assumed to be reheated to 90° C. before entering the membrane separation step. The second condensation step, 113, was assumed to be carried out at the same temperature as the first condensation step, again using cooling water.

The calculations were performed using differential element membrane code written at MTR and incorporated into a computer process simulation program (ChemCad 6.3, ChemStations, Austin, Tex.).

The results of the calculations are shown in Table 1.

TABLE 1

| Stream | 103 (feed) | 105 (condensate) | 108 | 111 | 112 | 114 (condensate) | 115 (off-gas) |
|---|---|---|---|---|---|---|---|
| Molar Flow (kmol/h) | 5,000 | 2,511 | 2,489 | 1,157 | 1,332 | 522 | 810 |
| Temp (° C.) | 134 | 15 | 90 | 92 | 94 | 15 | 15 |
| Pressure (bar) | 30 | 30 | 30 | 8 | 30 | 30 | 30 |
| Component (mol %) | | | | | | | |
| Hydrogen | 30.0 | 1.9 | 58.2 | 90.1 | 30.0 | 1.7 | 48.1 |
| Nitrogen | 1.3 | 0.2 | 2.5 | 1.4 | 3.4 | 0.4 | 5.4 |
| Carbon Monoxide | 0.7 | 0.1 | 1.4 | 1.3 | 1.5 | 0.2 | 2.4 |
| Methane | 1.8 | 0.6 | 3.0 | 1.0 | 4.7 | 1.3 | 6.8 |
| Ethane | 2.0 | 2.0 | 2.1 | 0.4 | 3.6 | 3.5 | 3.6 |
| Ethylene | 0.5 | 0.4 | 0.6 | 0.2 | 1.0 | 0.7 | 1.1 |
| Propane | 35.8 | 54.1 | 17.3 | 2.3 | 30.3 | 51.3 | 16.8 |
| Propylene | 26.7 | 38.7 | 14.7 | 2.6 | 25.0 | 39.9 | 15.6 |
| Iso-butane | 1.2 | 2.0 | 0.3 | 0.0 | 0.5 | 1.0 | 0.1 |

The process achieves 89.7% recovery of combined propane and propylene, without resorting to any condensation temperature lower than 15° C.

Example 2. Embodiment of FIG. 1, Applied to Iso-Butane Dehydrogenation

A calculation similar to that of Example 1 was performed to model the performance of the process of FIG. 1 in treating a raw product stream from an iso-butane dehydrogenation process. The stream flow rate was assumed to be 2,654 kmol/hour, and the molar composition was assumed to be approximately as follows:

Hydrogen: 33%

Iso-butane: 34%

Iso-butene: 28%

Other $C_4$s: 1%

$C_1$ and $C_2$: 1.3%

Other contaminants (nitrogen, CO, $C_3$): 2.6%.

It was further assumed that the raw product stream was compressed to 20 bara in compression step 102, then cooled using cooling water to 45° C. in first condensation step 104. The membrane was assumed to have a hydrogen permeance of 700 gpu, a hydrogen/iso-butane selectivity of 54 and a hydrogen/iso-butene selectivity of 47. The overhead stream from step 104 was assumed to be reheated to 90° C. before entering the membrane separation step. The second condensation step, 113, was assumed to be carried out at the same temperature as the first condensation step, again using cooling water.

The calculations were again performed using differential element membrane code written at MTR and incorporated into a computer process simulation program (ChemCad 6.3, ChemStations, Austin, Tex.).

The results of the calculations are shown in Table 2.

TABLE 2

| Stream | 103 feed | 105 condensate | 108 | 111 | 112 | 114 condensate | 115 off-gas |
|---|---|---|---|---|---|---|---|
| Molar Flow (kmol/h) | 2,654 | 1,234 | 1,419 | 692 | 727 | 294 | 434 |
| Temp (° C.) | 96 | 45 | 90 | 92 | 94 | 45 | 45 |
| Pressure (bar) | 20 | 20 | 20 | 8 | 20 | 20 | 20 |
| Component (mol %) | | | | | | | |
| Hydrogen | 33.0 | 1.4 | 60.2 | 89.0 | 32.8 | 1.3 | 54.2 |
| Nitrogen | 0.8 | 0.1 | 1.5 | 1.1 | 1.8 | 0.1 | 2.9 |
| Carbon Monoxide | 1.3 | 0.1 | 2.3 | 2.4 | 2.2 | 0.2 | 3.6 |
| Methane | 1.2 | 0.2 | 2.1 | 1.0 | 3.0 | 0.5 | 4.7 |
| Ethane | 0.1 | 0.0 | 0.1 | 0.1 | 0.2 | 0.1 | 0.2 |
| Ethylene | 0.0 | 0.0 | 0.1 | 0.1 | 0.1 | 0.0 | 0.1 |
| Propane | 0.3 | 0.3 | 0.2 | 0.1 | 0.4 | 0.5 | 0.4 |
| Propylene | 0.2 | 0.3 | 0.2 | 0.1 | 0.4 | 0.4 | 0.4 |
| Iso-butane | 34.2 | 52.0 | 18.7 | 3.3 | 33.4 | 53.9 | 19.6 |
| Iso-butene | 28.0 | 44.0 | 14.2 | 2.8 | 25.0 | 41.7 | 13.5 |
| Other C4 | 0.9 | 1.6 | 0.4 | 0.0 | 0.7 | 1.3 | 0.4 |

The process achieves 88.7% recovery of combined iso-butane and iso-butene, without resorting to any condensation temperature lower than 45° C.

Example 3. Embodiment of FIG. 2, Applied to Propane Dehydrogenation

A calculation was performed to model the performance of the process of FIG. 2 in treating a raw product stream from a propane dehydrogenation process. All assumptions regarding stream composition and operating conditions were the same as in Example 1. The results of the calculations are shown in Table 3.

TABLE 3

| Stream | 103 feed | 117 | 105 condensate | 108 | 111 | 112 | 116 recycle | 118 off-gas |
|---|---|---|---|---|---|---|---|---|
| Molar Flow (kmol/h) | 5,000 | 9,699 | 3,362 | 6,337 | 1,624 | 4.713 | 4,703 | 10 |
| Temp (° C.) | 134 | 117 | 15 | 90 | 91 | 92 | 92 | 92 |
| Pressure (bar) | 30 | 30 | 30 | 30 | 5 | 30 | 30 | 30 |
| Component (mol %) | | | | | | | | |
| Hydrogen | 29.9 | 31.0 | 1.6 | 46.5 | 88.6 | 32.0 | 32.0 | 32.0 |
| Nitrogen | 1.3 | 4.5 | 0.4 | 6.7 | 3.1 | 7.9 | 7.9 | 7.9 |
| Carbon Monoxide | 0.7 | 1.6 | 0.2 | 2.3 | 1.9 | 2.5 | 2.5 | 2.5 |
| Methane | 1.8 | 5.8 | 1.6 | 8.1 | 2.1 | 10.1 | 10.1 | 10.1 |
| Ethane | 2.1 | 2.9 | 2.9 | 3.0 | 0.4 | 3.9 | 3.9 | 3.9 |
| Ethylene | 0.5 | 0.8 | 0.6 | 1.0 | 0.3 | 1.2 | 1.2 | 1.2 |
| Propane | 35.8 | 29.4 | 52.3 | 17.2 | 1.6 | 22.6 | 22.6 | 22.6 |
| Propylene | 26.7 | 23.2 | 38.7 | 15.0 | 2.0 | 19.5 | 19.5 | 19.5 |
| Iso-butane | 1.2 | 0.8 | 1.7 | 0.2 | 0.0 | 0.3 | 0.3 | 0.3 |

Owing to the use of a recycle loop to return the hydrocarbon-enriched residue gas stream from the membrane separation step, the combined $C_3$ recovery increases to 97.9% with this process scheme.

Example 4. Embodiment of FIG. 2, Applied to Iso-Butane Dehydrogenation

A calculation was performed to model the performance of the process of FIG. 2 in treating a raw product stream from an iso-butane dehydrogenation process. All assumptions regarding stream composition and operating conditions were the same as in Example 2. The results of the calculations are shown in Table 4.

TABLE 4

| Stream | 103 feed | 117 | 105 con-densate | 108 | 111 | 112 | 116 recycle | 118 off-gas |
|---|---|---|---|---|---|---|---|---|
| Molar Flow (kmol/h) | 2,654 | 4,375 | 1,690 | 2,685 | 954 | 1,730 | 1,721 | 10 |
| Temp (° C.) | 96 | 95 | 45 | 90 | 91 | 93 | 93 | 93 |
| Pressure (bar) | 20 | 20 | 20 | 20 | 5 | 20 | 20 | 20 |
| Component (mol %) | | | | | | | | |
| Hydrogen | 32.9 | 32.5 | 1.2 | 52.2 | 88.9 | 32.0 | 32.0 | 32.0 |
| Nitrogen | 0.8 | 2.2 | 0.1 | 3.6 | 2.0 | 4.4 | 4.4 | 4.4 |
| Carbon Monoxide | 1.3 | 2.3 | 0.2 | 3.6 | 3.2 | 3.8 | 3.8 | 3.8 |
| Methane | 1.2 | 4.1 | 0.7 | 6.2 | 2.1 | 8.4 | 8.4 | 8.4 |
| Ethane | 0.1 | 0.2 | 0.1 | 0.2 | 0.0 | 0.3 | 0.3 | 0.3 |
| Ethylene | 0.0 | 0.1 | 0.1 | 0.1 | 0.0 | 0.2 | 0.2 | 0.2 |
| Propane | 0.3 | 0.4 | 0.4 | 0.3 | 0.0 | 0.5 | 0.5 | 0.5 |

TABLE 4-continued

| Stream | 103 feed | 117 | 105 con-densate | 108 | 111 | 112 | 116 recycle | 118 off-gas |
|---|---|---|---|---|---|---|---|---|
| Propylene | 0.2 | 0.3 | 0.3 | 0.3 | 0.1 | 0.4 | 0.4 | 0.4 |
| Iso-butane | 34.2 | 32.0 | 52.5 | 19.1 | 1.9 | 28.6 | 28.6 | 28.6 |
| Iso-butene | 28.0 | 25.2 | 43.0 | 14.0 | 1.7 | 20.8 | 20.8 | 20.8 |
| Other C4 | 1.0 | 0.9 | 1.4 | 0.4 | 0.1 | 0.6 | 0.6 | 0.6 |

As with Example 3, the use of a recycle loop to return the hydrocarbon-enriched residue gas stream from the membrane separation step increases the iso-butane plus iso-butene recovery to 97.7%.

Example 5. Embodiment of FIG. 3, Applied to Propane Dehydrogenation

A calculation was performed to model the performance of the process of FIG. 3 in treating a raw product stream from a propane dehydrogenation process. All assumptions regarding stream composition and operating conditions were the same as in Example 1. The results of the calculations are shown in Table 5.

TABLE 5

| Stream | 103 feed | 105 condensate | 108 | 111 | 112 | 114 condensate | 120 | 123 | 126 condensate | 127 off-gas |
|---|---|---|---|---|---|---|---|---|---|---|
| Molar Flow (kmol/h) | 5,000 | 2,510 | 2,489 | 1,119 | 1,370 | 527 | 842 | 254 | 127 | 461 |
| Temp (° C.) | 134 | 15 | 90 | 92 | 95 | 15 | 15 | 91 | 15 | 15 |
| Pressure (bar) | 30 | 30 | 30 | 5 | 30 | 30 | 30 | 5 | 30 | 30 |
| Component (mol %) | | | | | | | | | | |
| Hydrogen | 30.0 | 1.9 | 58.2 | 92.8 | 30.0 | 1.6 | 47.6 | 88.6 | 1.3 | 37.8 |
| Nitrogen | 1.3 | 0.2 | 2.5 | 1.1 | 3.6 | 0.4 | 5.7 | 2.7 | 0.6 | 8.7 |
| Carbon Monoxide | 0.7 | 0.1 | 1.4 | 1.1 | 1.6 | 0.2 | 2.6 | 2.1 | 0.3 | 3.4 |
| Methane | 1.8 | 0.6 | 3.0 | 0.8 | 4.8 | 1.3 | 6.9 | 1.9 | 2.2 | 11.0 |
| Ethane | 2.1 | 2.0 | 2.1 | 0.3 | 3.6 | 3.5 | 3.6 | 0.5 | 4.8 | 5.0 |
| Ethylene | 0.4 | 0.4 | 0.6 | 0.2 | 0.9 | 0.7 | 1.1 | 0.3 | 1.0 | 1.5 |
| Propane | 35.8 | 54.1 | 17.2 | 1.7 | 30.0 | 51.2 | 16.8 | 1.7 | 48.7 | 16.4 |
| Propylene | 26.7 | 38.7 | 14.7 | 2.0 | 25.0 | 40.1 | 15.6 | 2.2 | 40.5 | 16.1 |
| Iso-butane | 1.2 | 2.0 | 0.3 | 0.0 | 0.5 | 1.0 | 0.1 | 0.0 | 0.6 | 0.1 |

The process achieves 93.5% recovery of combined propane and propylene.

Example 6. Embodiment of FIG. 3. Applied to Iso-Butane Dehydrogenation

A calculation was performed to model the performance of the process of FIG. 3 in treating a raw product stream from an iso-butane dehydrogenation process. All assumptions regarding stream composition and operating conditions were the same as in Example 2. The results of the calculations are shown in Table 6.

TABLE 6

| Stream | 103 feed | 105 condensate | 108 | 111 | 112 | 114 condensate | 120 | 123 | 126 condensate | 127 off-gas |
|---|---|---|---|---|---|---|---|---|---|---|
| Molar Flow (kmol/h) | 2,654 | 1,234 | 1,419 | 692 | 727 | 294 | 434 | 177 | 77 | 179 |

TABLE 6-continued

| Stream | 103 feed | 105 condensate | 108 | 111 | 112 | 114 condensate | 120 | 123 | 126 condensate | 127 off-gas |
|---|---|---|---|---|---|---|---|---|---|---|
| Temp (° C.) | 96 | 45 | 90 | 92 | 93 | 45 | 90 | 91 | 45 | 45 |
| Pressure (bar) | 20 | 20 | 20 | 8 | 20 | 20 | 20 | 8 | 20 | 20 |
| Component (mol %) | | | | | | | | | | |
| Hydrogen | 32.9 | 1.4 | 60.2 | 89.0 | 32.8 | 1.3 | 54.2 | 85.0 | 1.1 | 46.5 |
| Nitrogen | 0.8 | 0.1 | 1.5 | 1.1 | 1.8 | 0.1 | 3.0 | 2.3 | 0.2 | 4.8 |
| Carbon Monoxide | 1.3 | 0.1 | 2.3 | 2.4 | 2.2 | 0.2 | 3.6 | 3.9 | 0.2 | 4.8 |
| Methane | 1.2 | 0.2 | 2.0 | 1.0 | 3.0 | 0.5 | 4.7 | 2.3 | 0.9 | 8.6 |
| Ethane | 0.1 | 0.0 | 0.1 | 0.1 | 0.2 | 0.1 | 0.2 | 0.1 | 0.2 | 0.4 |
| Ethylene | 0.0 | 0.0 | 0.1 | 0.1 | 0.1 | 0.0 | 0.1 | 0.1 | 0.1 | 0.2 |
| Propane | 0.3 | 0.3 | 0.3 | 0.1 | 0.4 | 0.5 | 0.4 | 0.1 | 0.7 | 0.6 |
| Propylene | 0.2 | 0.3 | 0.2 | 0.1 | 0.4 | 0.4 | 0.4 | 0.1 | 0.6 | 0.5 |
| Iso-butane | 34.2 | 52.0 | 18.7 | 3.3 | 33.4 | 53.9 | 19.5 | 3.4 | 55.1 | 20.2 |
| Iso-butene | 28.0 | 44.0 | 14.2 | 2.8 | 24.9 | 41.7 | 13.5 | 2.7 | 39.8 | 13.1 |
| Other C4 | 1.0 | 1.6 | 0.4 | 0.0 | 0.8 | 1.3 | 0.4 | 0.0 | 1.1 | 0.3 |

The process achieves 93.1% recovery of combined iso-butane and iso-butene.

Example 7. Embodiment of FIG. 4, Applied to Propane Dehydrogenation

A calculation was performed to model the performance of the process of FIG. 4 in treating a raw product stream from a propane dehydrogenation process. All assumptions regarding stream composition and operating conditions were the same as in Example 1. In addition, the uncondensed gas from condensation step 113 was assumed to be provided as feed to the hydrocarbons-selective membrane separation step, 128, without pressure or temperature adjustment, and this step was assumed to be carried out using a membrane having propane and propylene permeances of 650 gpu, and propane/hydrogen and propylene/hydrogen selectivity of 4.5.

The results of the calculations are shown in Table 7.

In similar manner to the embodiment of FIG. 2, the use of a recycle loop to return permeate gas from the hydrocarbon-selective membranes results in a very high combined recovery of propane and propylene of 98.0%.

Example 8. Embodiment of FIG. 4, Applied to Iso-Butane Dehydrogenation

A calculation was performed to model the performance of the process of FIG. 4 in treating a raw product stream from an iso-butane dehydrogenation process. All assumptions regarding stream composition and operating conditions were the same as in Example 2. In addition, the uncondensed gas from condensation step 113 was assumed to be provided as feed to the hydrocarbons-selective membrane separation step, 128, without pressure or temperature adjustment, and this step was assumed to be carried out using a membrane having iso-butane and iso-butene permeances of 1,535 gpu, and iso-butane/hydrogen and iso-butene/hydrogen selectivity of 11.

TABLE 7

| Stream | 103 feed | 105 condensate | 108 | 111 | 112 | 114 condensate | 115 | 132 recycle | 134 off-gas |
|---|---|---|---|---|---|---|---|---|---|
| Molar Flow (kmol/h) | 5,000 | 2,666 | 3,715 | 1,425 | 2,291 | 686 | 1,604 | 1,382 | 222 |
| Temp (° C.) | 134 | 15 | 90 | 92 | 94 | 15 | 15 | 138 | −8 |
| Pressure (bar) | 30 | 30 | 30 | 5 | 30 | 30 | 30 | 30 | 30 |
| Component (mol %) | | | | | | | | | |
| Hydrogen | 30.0 | 1.8 | 53.4 | 91.0 | 30 | 1.5 | 42.1 | 38.6 | 63.6 |
| Nitrogen | 1.3 | 0.2 | 3.0 | 1.4 | 4.0 | 0.3 | 5.5 | 3.6 | 17.3 |
| Carbon Monoxide | 0.7 | 0.1 | 2.0 | 1.6 | 2.2 | 0.2 | 3.1 | 2.9 | 4.3 |
| Methane | 1.8 | 1.2 | 5.9 | 1.6 | 8.6 | 2.2 | 11.3 | 11.7 | 9.0 |
| Ethane | 2.1 | 2.6 | 2.6 | 0.4 | 4.0 | 4.0 | 4.1 | 4.6 | 1.2 |
| Ethylene | 0.5 | 0.5 | 0.8 | 0.2 | 1.2 | 0.9 | 1.3 | 1.5 | 0.4 |
| Propane | 35.8 | 53.1 | 17.1 | 1.7 | 26.8 | 50.3 | 16.8 | 19.1 | 2.2 |
| Propylene | 26.7 | 38.6 | 15.0 | 2.1 | 22.8 | 39.6 | 15.6 | 17.8 | 2.0 |
| Iso-butane | 1.1 | 1.9 | 0.2 | 0.0 | 1.4 | 1.0 | 0.2 | 0.2 | 0.0 |

The results of the calculations are shown in Table 8.

TABLE 8

| Stream | 103 feed | 105 condensate | 108 | 111 | 112 | 114 condensate | 115 | 132 recycle | 134 off-gas |
|---|---|---|---|---|---|---|---|---|---|
| Molar Flow (kmol/h) | 2,653 | 1,310 | 1,776 | 809 | 967 | 377 | 591 | 433 | 158 |
| Temp (° C.) | 96 | 45 | 90 | 92 | 94 | 45 | 45 | 124 | 34 |
| Pressure (bar) | 20 | 20 | 20 | 5 | 20 | 20 | 20 | 22 | 20 |
| Component (mol %) | | | | | | | | | |
| Hydrogen | 32.9 | 1.3 | 57.9 | 91.3 | 30.0 | 1.2 | 48.3 | 40.1 | 71.0 |
| Nitrogen | 0.8 | 0.1 | 1.6 | 0.9 | 2.2 | 0.1 | 3.5 | 1.9 | 7.9 |
| Carbon Monoxide | 1.3 | 0.1 | 2.9 | 2.6 | 3.1 | 0.2 | 4.9 | 4.2 | 6.9 |
| Methane | 1.2 | 0.4 | 3.5 | 1.2 | 5.3 | 0.9 | 8.3 | 8.2 | 8.6 |
| Ethane | 0.1 | 0.1 | 0.1 | 0.0 | 0.2 | 0.1 | 0.3 | 0.3 | 0.2 |
| Ethylene | 0.0 | 0.0 | 0.1 | 0.1 | 0.1 | 0.1 | 0.2 | 0.2 | 0.1 |
| Propane | 0.3 | 0.4 | 0.3 | 0.1 | 0.5 | 0.6 | 0.4 | 0.5 | 0.2 |
| Propylene | 0.2 | 0.3 | 0.3 | 0.1 | 0.4 | 0.5 | 0.4 | 0.5 | 0.2 |
| Iso-butane | 34.2 | 52.3 | 18.8 | 2.0 | 33.0 | 53.7 | 19.7 | 25.8 | 2.9 |
| Iso-butene | 28.0 | 43.6 | 14.1 | 1.7 | 24.4 | 41.3 | 13.6 | 17.7 | 2.0 |
| Other C4 | 1.0 | 1.4 | 0.4 | 0.0 | 0.8 | 1.3 | 0.4 | 0.6 | 0.0 |

As with Example 7, the use of a recycle loop to return the hydrocarbon-enriched permeate gas stream from the membrane separation step increases the iso-butane plus iso-butene recovery to 97.8%.

Example 9. Embodiment of FIG. 5, Applied to Propane Dehydrogenation

A calculation was performed to model the performance of the process of FIG. 5 in treating a raw product stream from a propane dehydrogenation process. All assumptions regarding stream composition and operating conditions were the same as in Examples 1 and 7.

The results of the calculations are shown in Table 9.

TABLE 9

| Stream | 503 feed | 506 condensate | 511 | 514 | 515 recycle | 509 | 518 recycle | 521 off-gas |
|---|---|---|---|---|---|---|---|---|
| Molar Flow (kmol/h) | 5,000 | 3,364 | 5,565 | 1,624 | 3,941 | 80 | 66 | 14 |
| Temp (° C.) | 134 | 15 | 90 | 91 | 96 | 15 | 4 | −6 |
| Pressure (bar) | 30 | 30 | 30 | 5 | 32 | 30 | 3 | 30 |
| Component (mol %) | | | | | | | | |
| Hydrogen | 30.0 | 1.6 | 46.9 | 88.3 | 30.0 | 47.0 | 42.2 | 69.5 |
| Nitrogen | 1.3 | 0.4 | 6.4 | 3.1 | 7.8 | 6.3 | 3.9 | 17.9 |
| Carbon Monoxide | 0.7 | 0.2 | 2.3 | 1.9 | 2.5 | 2.3 | 2.1 | 3.2 |
| Methane | 1.8 | 1.5 | 8.0 | 2.2 | 10.4 | 8.0 | 8.3 | 6.7 |
| Ethane | 2.1 | 2.9 | 3.0 | 0.4 | 4.0 | 3.0 | 3.5 | 0.5 |
| Ethylene | 0.4 | 0.6 | 1.0 | 0.3 | 1.2 | 1.0 | 1.1 | 0.1 |
| Propane | 35.8 | 52.4 | 17.2 | 1.7 | 23.6 | 17.2 | 20.6 | 1.1 |
| Propylene | 26.8 | 38.7 | 15.0 | 2.1 | 20.4 | 15.0 | 18.0 | 1.0 |
| Iso-butane | 1.1 | 1.7 | 0.2 | 0.0 | 0.3 | 0.2 | 0.3 | 0.0 |

In this embodiment, both the residue gas from the hydrogen-selective membrane separation step and the permeate gas from the hydrocarbon-selective membrane separation step are recycled within the process. The process results in a very high combined recovery of propane and propylene of 98.0%.

Example 10. Embodiment of FIG. 5, Applied to Iso-Butane Dehydrogenation

A calculation was performed to model the performance of the process of FIG. 5 in treating a raw product stream from an iso-butane dehydrogenation process. All assumptions regarding stream composition and operating conditions were the same as in Examples 2 and 8.

The results of the calculations are shown in Table 10.

TABLE 10

| Stream | 503 feed | 506 condensate | 511 | 514 | 515 recycle | 509 | 518 recycle | 521 off-gas |
|---|---|---|---|---|---|---|---|---|
| Molar Flow (kmol/h) | 2,654 | 1,729 | 1,676 | 922 | 754 | 10 | 6 | 4 |
| Temp (° C.) | 120 | 50 | 90 | 94 | 100 | 50 | 44 | 38 |
| Pressure (bar) | 31 | 31 | 31 | 5 | 33 | 31 | 4 | 31 |
| Component (mol %) | | | | | | | | |
| Hydrogen | 32.8 | 2.2 | 59.5 | 90.1 | 22.1 | 59.5 | 48.3 | 80.0 |
| Nitrogen | 0.8 | 0.2 | 3.7 | 2.0 | 5.7 | 3.6 | 1.8 | 6.9 |
| Carbon Monoxide | 1.3 | 0.5 | 3.8 | 3.2 | 4.5 | 3.8 | 3.2 | 4.8 |
| Methane | 1.2 | 0.9 | 5.6 | 1.8 | 10.3 | 5.6 | 5.7 | 5.4 |
| Ethane | 0.1 | 0.1 | 0.1 | 0.0 | 0.3 | 0.2 | 0.2 | 0.1 |
| Ethylene | 0.0 | 0.1 | 0.1 | 0.0 | 0.2 | 0.1 | 0.1 | 0.1 |
| Propane | 0.3 | 0.4 | 0.2 | 0.0 | 0.5 | 0.2 | 0.3 | 0.1 |
| Propylene | 0.2 | 0.3 | 0.2 | 0.1 | 0.5 | 0.2 | 0.3 | 0.1 |
| Iso-butane | 34.2 | 51.7 | 15.1 | 1.4 | 31.8 | 15.1 | 22.6 | 1.4 |
| Iso-butene | 28.0 | 42.3 | 11.1 | 1.2 | 23.2 | 11.1 | 16.7 | 1.0 |
| Other C4 | 1.0 | 1.4 | 0.4 | 0.0 | 0.7 | 0.5 | 0.6 | 0.0 |

As with Example 9, a high iso-butane plus iso-butene recovery of 98.0% is achieved.

Example 11. Embodiment of FIG. 6, Applied to Propane Dehydrogenation

A calculation was performed to model the performance of the process of FIG. 6 in treating a raw product stream from a propane dehydrogenation process. All assumptions regarding stream composition and operating conditions were the same as in Examples 1 and 7.

As shown in FIG. 6, the hydrogen-rich permeate stream from membrane separation step 611 was assumed to be compressed and sent to pressure swing adsorption (PSA), and the tail gas from regeneration of the PSA beds was assumed to be recompressed to a slight overpressure of 33 bara and returned for reprocessing in step 611.

The results of the calculations are shown in Table 11.

TABLE 11

| Stream | 603 feed | 606 condensate | 610 | 618 | 620 condensate | 613 to PSA | 628 | 617 | 627 off-gas | 624 recycle |
|---|---|---|---|---|---|---|---|---|---|---|
| Molar Flow (kmol/h) | 5,000 | 2,750 | 4,589 | 3,030 | 679 | 1,560 | 1,247 | 313 | 323 | 2,027 |
| Temp (° C.) | 134 | 15 | 90 | 93 | 15 | 91 | 343 | 238 | −9 | 3 |
| Pressure (bar) | 30 | 30 | 30 | 30 | 30 | 5 | 33 | 33 | 30 | 5 |
| Component (mol %) | | | | | | | | | | |
| Hydrogen | 30.0 | 1.7 | 50.0 | 30.0 | 1.3 | 88.8 | 99.9 | 44.2 | 60.3 | 34.7 |
| Nitrogen | 1.3 | 0.2 | 3.5 | 4.4 | 0.4 | 1.6 | 0.0 | 8.1 | 17.9 | 3.6 |
| Carbon Monoxide | 0.7 | 0.2 | 4.2 | 4.6 | 0.4 | 3.4 | 0.0 | 16.8 | 8.5 | 5.3 |
| Methane | 1.8 | 1.4 | 7.3 | 10.1 | 2.4 | 2.0 | 0.0 | 9.8 | 10.4 | 12.6 |
| Ethane | 2.1 | 2.7 | 2.8 | 4.0 | 3.8 | 0.4 | 0.0 | 1.9 | 0.6 | 4.6 |
| Ethylene | 0.5 | 0.6 | 0.9 | 1.3 | 1.0 | 0.2 | 0.0 | 1.3 | 0.2 | 1.6 |
| Propane | 35.8 | 52.6 | 16.5 | 24.2 | 50.0 | 1.6 | 0.0 | 7.9 | 1.1 | 19.3 |
| Propylene | 26.7 | 38.7 | 14.6 | 21.1 | 39.6 | 2.0 | 0.0 | 9.9 | 1.0 | 18.1 |
| Iso-butane | 1.1 | 1.9 | 0.2 | 0.3 | 1.1 | 0.0 | 0.0 | 0.1 | 0.0 | 0.2 |

Return of the tail gas from the PSA step, in conjunction with recycle of the permeate from membrane separation step 622, results in a combined recovery of propane and propylene of 99.8%. In addition, a stream of essentially pure hydrogen is produced.

Example 12. Embodiment of FIG. 6, Applied to Iso-Butane Dehydrogenation

A calculation was performed to model the performance of the process of FIG. 6 in treating a raw product stream from an iso-butane dehydrogenation process. All assumptions regarding stream composition and operating conditions were the same as in Examples 2 and 8.

As shown in FIG. 6, the hydrogen-rich permeate stream from membrane separation step 611 was assumed to be compressed and sent to pressure swing adsorption (PSA), and the tail gas from regeneration of the PSA beds was assumed to be recompressed to a slight overpressure of 33 bara and returned for reprocessing in step 611.

The results of the calculations are shown in Table 12.

TABLE 12

| Stream | 603 feed | 606 condensate | 610 | 618 | 620 condensate | 613 to PSA | 628 | 617 | 627 off-gas | 624 recycle |
|---|---|---|---|---|---|---|---|---|---|---|
| Molar Flow (kmol/h) | 2,654 | 1,354 | 2,435 | 1,544 | 372 | 891 | 707 | 184 | 221 | 951 |
| Temp (° C.) | 96 | 45 | 90 | 93 | 45 | 91 | 343 | 225 | 33 | 39 |
| Pressure (bar) | 20 | 20 | 20 | 20 | 20 | 5 | 33 | 33 | 20 | 5 |

TABLE 12-continued

| Stream | 603 feed | 606 condensate | 610 | 618 | 620 condensate | 613 to PSA | 628 | 617 | 627 off-gas | 624 recycle |
|---|---|---|---|---|---|---|---|---|---|---|
| Component (mol %) | | | | | | | | | | |
| Hydrogen | 32.9 | 1.3 | 53.0 | 32.9 | 1.0 | 88.0 | 99.8 | 42.7 | 65.7 | 37.6 |
| Nitrogen | 0.8 | 0.1 | 2.0 | 2.6 | 0.1 | 1.1 | 0 | 5.2 | 9.1 | 2.1 |
| Carbon Monoxide | 1.3 | 0.2 | 6.6 | 7.1 | 0.4 | 5.8 | 0.1 | 27.6 | 13.3 | 8.3 |
| Methane | 1.2 | 0.6 | 5.3 | 7.4 | 1.0 | 1.7 | 0.1 | 8.1 | 9.1 | 9.6 |
| Ethane | 0.1 | 0.1 | 0.2 | 0.3 | 0.1 | 0.0 | 0.0 | 0.1 | 0.1 | 0.3 |
| Ethylene | 0.0 | 0.0 | 0.2 | 0.2 | 0.1 | 0.1 | 0.0 | 0.2 | 0.1 | 0.2 |
| Propane | 0.3 | 0.4 | 0.3 | 0.4 | 0.5 | 0.0 | 0.0 | 0.2 | 0.1 | 0.5 |
| Propylene | 0.2 | 0.3 | 0.3 | 0.4 | 0.5 | 0.1 | 0.0 | 0.2 | 0.1 | 0.5 |
| Iso-butane | 34.2 | 52.3 | 18.2 | 27.7 | 53.1 | 1.7 | 0.0 | 8.4 | 1.4 | 23.8 |
| Iso-butene | 28.0 | 43.3 | 13.5 | 20.5 | 41.8 | 1.5 | 0.0 | 7.2 | 1.0 | 16.7 |
| Other C4 | 1.0 | 1.4 | 0.4 | 0.5 | 1.4 | 0.0 | 0.0 | 0.1 | 0.0 | 0.4 |

Return of the tail gas from the PSA step, in conjunction with recycle of the permeate from membrane separation step 622, results in a combined recovery of iso-butane and iso-butene of 99.7%. In addition, a stream of essentially pure hydrogen is produced.

Example 13. Embodiment of FIG. 2, Applied to Propane Dehydrogenation at Low Temperature and Pressure A calculation was performed to model the performance of the process of FIG. 2 in treating a raw product stream from a propane dehydrogenation process at a lower temperature and lower pressure than the previously described examples. It was assumed that that the raw product stream was compressed to 13.7 bara in compression step 102, then cooled using a refrigerant to −5° C. in first condensation step 104. All other assumptions regarding stream composition and operating conditions were the same as in Example 1. The results of the calculations are shown in Table 13.

TABLE 13

| Stream | 103 (feed) | 117 | 105 (condensate) | 108 | 111 | 112 | 116 (recycle) | 118 (off-gas) |
|---|---|---|---|---|---|---|---|---|
| Molar Flow (kmol/h) | 5,000 | 12,862 | 3,248 | 9,615 | 1,715 | 7,899 | 7,889 | 10 |
| Temp (° C.) | 82 | 89 | −5 | 90 | 90 | 91 | 91 | 91 |
| Pressure (bar) | 13.7 | 13.7 | 13.7 | 13.7 | 13.7 | 13.7 | 13.7 | 13.7 |
| Component (mol %) | | | | | | | | |
| Hydrogen | 29.9 | 31.2 | 0.5 | 41.6 | 85.6 | 32.0 | 32.0 | 32.0 |
| Nitrogen | 1.3 | 4.6 | 0.2 | 6.7 | 3.4 | 6.7 | 6.7 | 6.7 |
| Carbon Monoxide | 0.7 | 1.6 | 0.1 | 2.1 | 2.0 | 2.1 | 2.1 | 2.1 |
| Methane | 1.8 | 7.3 | 1.0 | 9.4 | 3.0 | 10.8 | 10.8 | 10.8 |
| Ethane | 2.1 | 3.6 | 2.8 | 3.9 | 0.6 | 4.6 | 4.6 | 4.6 |
| Ethylene | 0.5 | 1.0 | 0.5 | 1.2 | 0.4 | 1.4 | 1.4 | 1.4 |
| Propane | 35.8 | 27.5 | 53.7 | 18.7 | 2.2 | 22.3 | 22.3 | 22.3 |
| Propylene | 26.7 | 22.5 | 39.5 | 16.8 | 2.8 | 19.9 | 19.9 | 19.9 |
| Iso-butane | 1.2 | 0.6 | 1.8 | 0.2 | 0.0 | 0.3 | 0.3 | 0.3 |

Operating at a lower temperature and a lower pressure than the conditions of Example 3, this process achieves 96.8% recovery of combined propane and propylene.

We claim:

1. A process for treating a raw product stream from dehydrogenation of a light paraffin, the raw product stream comprising at least one paraffin component, one olefin component and hydrogen, comprising the steps of:
    (a) compressing the raw product stream to create a compressed stream having a first hydrocarbon dewpoint;
    (b) partially condensing the compressed stream, including cooling and separating the compressed stream into a hydrocarbon condensate stream and an uncondensed gas stream;
    (c) withdrawing a first portion of the uncondensed gas stream as a purge stream;
    (d) heating a second portion of the uncondensed gas stream;
    (e) separating the second portion of the uncondensed gas stream from step (d) using a first membrane to remove a hydrogen-rich permeate gas stream and create a hydrocarbon-enriched residue gas stream having a first residue hydrocarbon dewpoint;
    (f) recirculating the hydrocarbon-enriched residue gas stream back to a point in the process upstream of step (b);
    (g) separating the purge stream from step (c) using a second membrane to remove a hydrocarbon-rich permeate gas stream and a hydrocarbon-depleted residue gas stream;
    (h) discharging the hydrocarbon-depleted residue gas stream as a treated purge gas stream; and
    (i) recirculating the hydrocarbon-rich permeate gas stream back to a point in the process upstream of step (b).

2. The process of claim 1, wherein the olefin component is propylene.

3. The process of claim 1, wherein the olefin component is iso-butene.

4. The process of claim 1, wherein the first residue hydrocarbon dewpoint is within 15° C. of the first hydrocarbon dewpoint.

5. The process of claim 1, wherein the membrane of step (e) has a hydrogen permeance of at least 200 gpu.

6. The process of claim 1, wherein the membrane of step (e) has a selectivity of hydrogen over propylene of at least 30.

7. The process of claim 1, wherein the membrane of step (e) has a selectivity of hydrogen over iso-butene of at least 100.

8. A process for treating a raw product stream from dehydrogenation of a light paraffin, the raw product stream comprising at least one paraffin component, one olefin component and hydrogen, comprising the step of:
(a) compressing the raw product stream to create a compressed stream having a first hydrocarbon dewpoint;
(b) partially condensing the compressed stream, including cooling and separating the compressed stream into a hydrocarbon condensate stream and an uncondensed gas stream;
(c) withdrawing a first portion of the uncondensed gas stream as a purge stream;
(d) heating a second portion of the uncondensed gas stream;
(e) separating the second portion of the uncondensed gas stream from step (d) using a first membrane to remove a hydrogen-rich permeate gas stream and create a hydrocarbon-enriched residue gas stream having a first residue hydrocarbon dewpoint;
(f) recirculating the hydrocarbon-enriched residue gas stream back to a point in the process upstream of step (b);
(g) separating the purge stream from step (c) using a second membrane to remove a hydrocarbon-rich permeate gas stream and a hydrocarbon-depleted residue gas stream;
(h) discharging the hydrocarbon-depleted residue gas stream as a treated purge gas stream;
(i) recirculating the hydrocarbon-rich permeate gas stream back to a point in the process upstream of step (b); and
(j) compressing the hydrocarbon-rich permeate gas stream prior to step (b).

9. A process for treating a raw product stream from dehydrogenation of a light paraffin, said raw product stream comprising at least one paraffin component, one olefin component and hydrogen, comprising the steps of:
(a) compressing the raw product stream to create a compressed stream having a first hydrocarbon dewpoint;
(b) partially condensing the compressed stream, including cooling and separating the compressed stream into a first hydrocarbon condensate stream and a first uncondensed gas stream;
(c) heating the first uncondensed gas stream from step (b);
(d) separating the first uncondensed gas stream from step (c) using a first membrane to remove a first hydrogen-rich permeate gas stream and create a first hydrocarbon-enriched residue gas stream having a first residue hydrocarbon dewpoint;
(e) partially condensing the first hydrocarbon-enriched residue gas stream, including cooling and separating the first hydrocarbon-enriched residue gas stream into a second hydrocarbon condensate and a second uncondensed gas stream;
(f) heating the second uncondensed gas stream from step (e);
(g) separating the second uncondensed gas stream from step (f) using a second membrane to remove a second hydrogen-rich permeate gas stream and create a second hydrocarbon-enriched residue gas stream having a second residue hydrocarbon dewpoint; and
(h) partially condensing the second hydrocarbon-enriched residue gas stream, including cooling and separating the second residue gas stream into a third hydrocarbon condensate and a third uncondensed gas stream.

10. The process of claim 9, wherein the olefin component is propylene.

11. The process of claim 9, wherein the olefin component is iso-butene.

12. The process of claim 9, wherein steps (b), (e) and (h) use a water coolant.

13. The process of claim 9, wherein steps (b), (e) and (h) use a refrigerant coolant.

14. The process of claim 9, wherein steps (b), (e) and (h) reduce the dewpoint of the compressed stream, the first hydrocarbon-enriched residue gas stream, and the second hydrocarbon-enriched residue gas stream, respectively, between 20° C. and 50° C.

15. The process of claim 9, wherein steps (d) and (g) increase the dewpoint of the first hydrocarbon-enriched residue stream and the second hydrocarbon-enriched residue stream, respectively, between 20° C. and 50° C.

16. The process of claim 9, wherein the first residue hydrocarbon dewpoint and the second residue hydrocarbon dewpoint are within 15° C. of the first hydrocarbon dewpoint.

17. The process of claim 9, wherein the compressed steam, the first hydrocarbon-enriched residue stream, and the second hydrocarbon-enriched residue stream are cooled to a temperature no lower than −30° C.

18. The process of claim 9, wherein the first and second membranes have a hydrogen permeance of at least 200 gpu.

19. The process of claim 9, wherein the first and second membranes have a selectivity of hydrogen over propylene of at least 30.

20. The process of claim 9, wherein the first and second membranes have a selectivity of hydrogen over iso-butene of at least 100.

* * * * *